Figure 1:
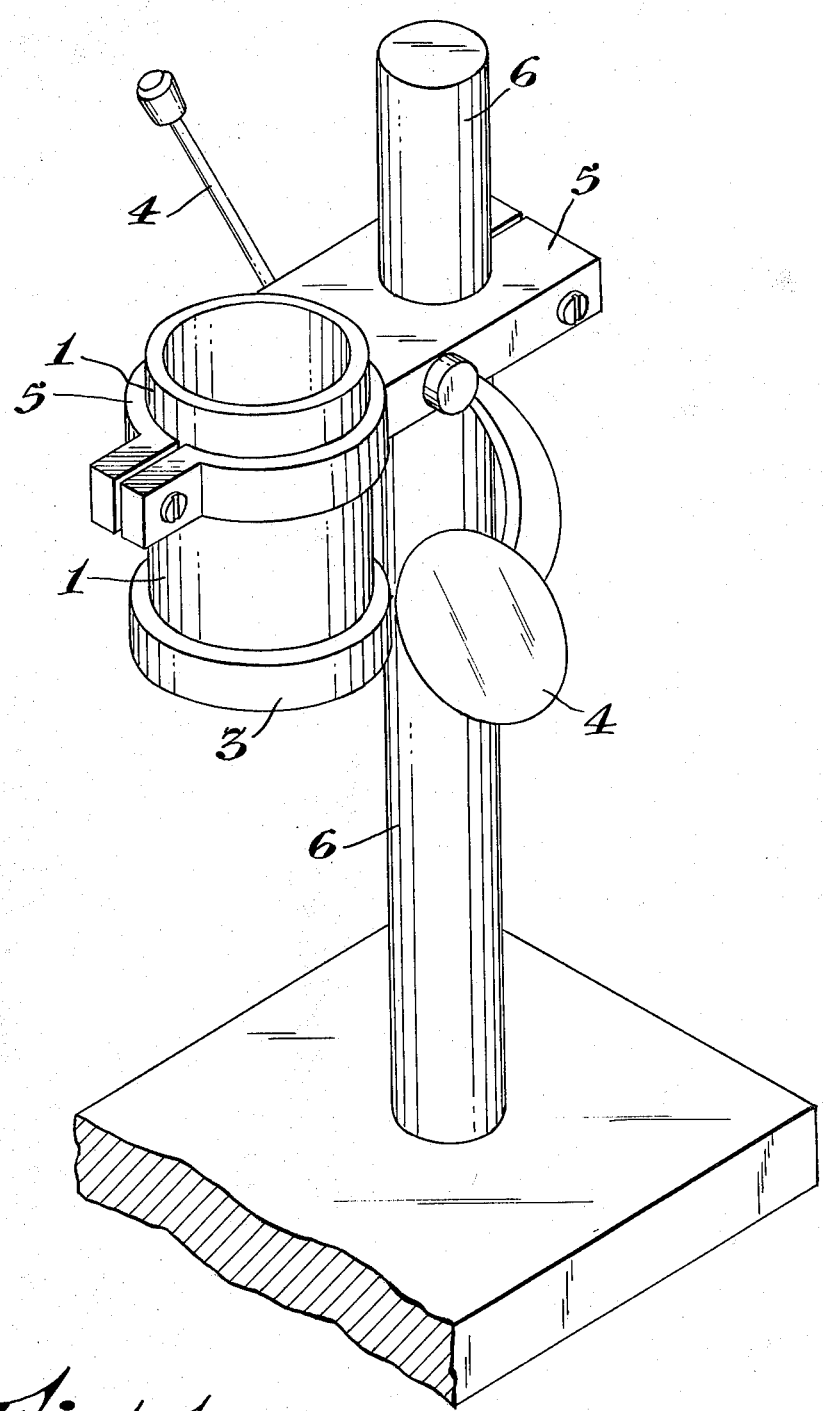

United States Patent [19]

Gioia

[11] 4,274,286
[45] Jun. 23, 1981

[54] POWDER FLOWABILITY TEST EQUIPMENT

[75] Inventor: Alberto Gioia, Como, Italy
[73] Assignee: Gruppo Lepetit S.p.A., Milan, Italy
[21] Appl. No.: 64,150
[22] Filed: Aug. 6, 1979
[51] Int. Cl.³ ............................................. G01N 11/04
[52] U.S. Cl. ................................................... 73/432 R
[58] Field of Search ..................................... 73/432 R
[56] References Cited

U.S. PATENT DOCUMENTS 3,376,753 4/1968 Pitkin et al. ....................... 73/432 R

OTHER PUBLICATIONS

Ausberger et al., J. Pharm. Sci. 55, No. 4, 418-422, (1966).
Nelson, J. Am. Pharm. Asso. Sci. Ed. 44, No. 7, 435-437, (1955).
Train, J. Pharm. Pharnol. 10, 127T-135T, (1958).
Hammerness et al., J. Am. Pharm. Asso. Sci. Ed. 47, No. 1, 58-61, (1955).
Gold et al., J. Pharm. Sci. 55, Noll 1291-1292, (1966) and No. 10, 1133-1136, (1966).
Degrussa, Technical Bulletin No. 31.
Shangraw, Pre-Conference Study Guide for Fifth Annual Educational Conference for Industrial Pharmacists.

*Primary Examiner*—S. Clement Swisher

[57] ABSTRACT

An apparatus for measuring the flowability of powder utilizes a container having a bottom wall with an opening therein. The bottom wall may be changed to provide openings of different sizes. The test consists of allowing the powder to flow through successively smaller holes. The smallest hole size through which the powder will freely flow is a measure of its flowability.

9 Claims, 6 Drawing Figures

U.S. Patent    Jun. 23, 1981    Sheet 1 of 3    4,274,286

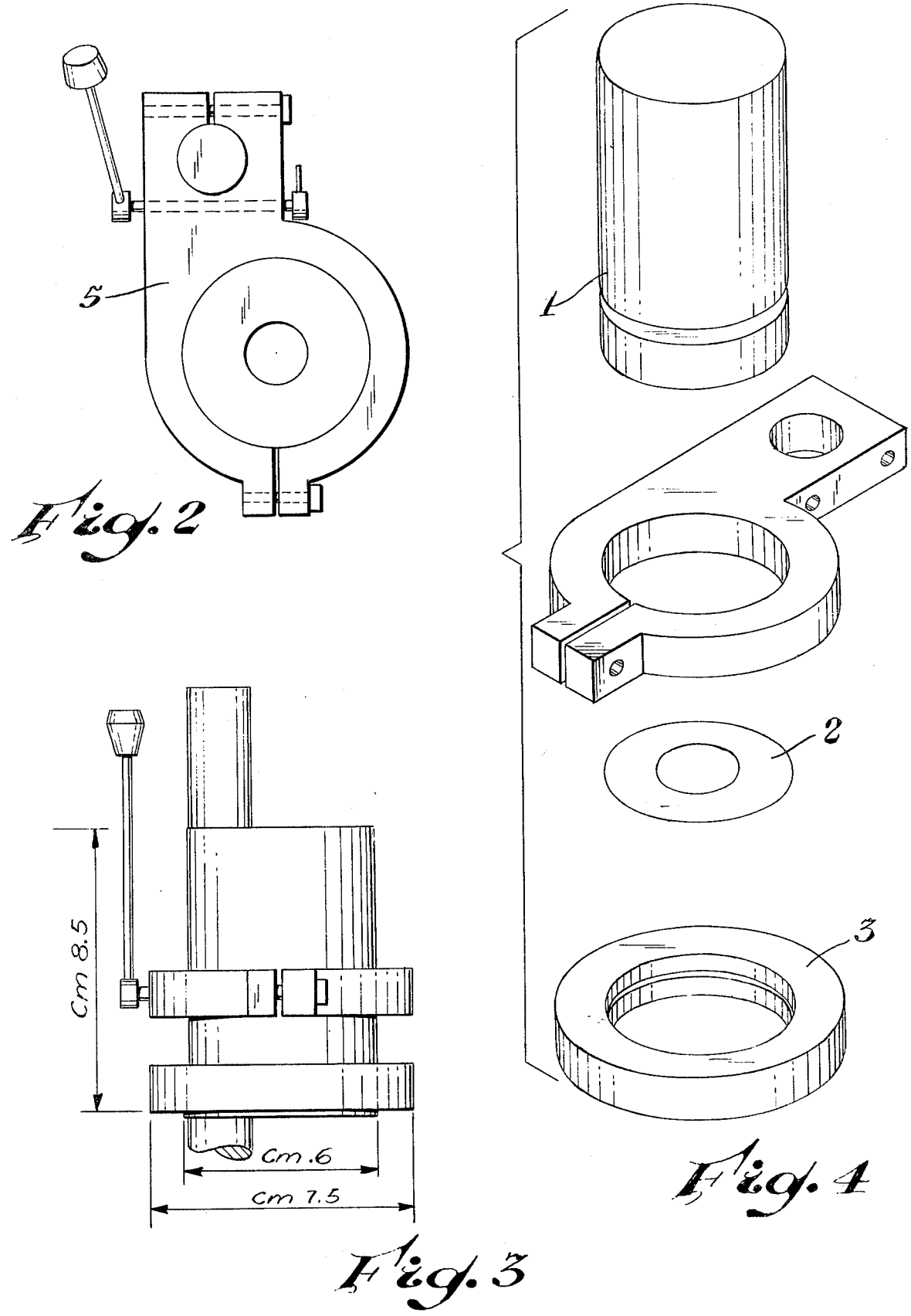

POWDER FLOWABILITY TEST EQUIPMENT

BACKGROUND OF THE INVENTION

Powder flowability can be defined as the property of the powder to flow evenly from the top to the bottom of the hopper and then to the dosage, compact and crush chamber under the influence of gravity force and other forces. Poorly flowing powders present many difficulties in the pharmaceutical industry both in compressed tablet manufacturing and in capsule filling operations. A free-flowing powder on the other hand offers many advantages which, for instance in case of the manufacture of compressed tablet, can be summarized as follows:

(a) The powder easily flows in the hopper without forming air pockets;

(b) The die cavity is filled more efficiently, and this is reflected in an increase of the mean tablet weight and a decrease of the coefficient of variation, due to lack of low dosing;

(c) As a consequence of the uniform tablet weights and uniform doses of active ingredients, also other parameters of the finished tablets, such as hardness, friability, disintegrating time, dissolution test and plasma levels are reproducible;

(d) Another consequence of the more efficient die cavity filling will be reflected in the uniformity of the compressing power and therefore less wear of the machine;

(e) Since a free-flowing powder also has a good permeability, it will result in an easy ejection of air during the compression and therefore fewer defective tablets due to capping or splitting;

(f) High production rate allowed by the high flow rate of a free-flowing powder.

In view of this, many efforts have been made recently to overcome problems created by poor-flow properties by studying different formulations and applying different manufacturing techniques. At the same time many attempts have been made to establish experimental procedures having practical industrial significance which can really measure or assess the intrinsic flowability of the powder to be incapsulated or compressed. A number of authors identified the powder flowability with the interparticulate friction, of which the "angle of repose" is a manifestation (E. Nelson - J. Am. Pharm. Assoc. Sci. Ed. 44, No. 7, 435–437 (1955)) and at least four practical methods of measuring the angle of repose have been developed which are described and compared by David Train in J. Pharm. Pharmacol. 10, 127T to 135T (1958).

Basically, according to the "angle of repose" method the powdered material is allowed to fall freely through an orifice onto a flat surface to form a conical pile of the deposited material and the angle between the surface of the cone and the horizontal plane is known as the angle of repose. A high angle would indicate a poorly flowing material whereas a low angle would indicate good flow.

Timed delivery through an orifice is an other method often used for evaluating the flowability of materials. A stop watch is usually used to either time a certain weights of powder flowing through the orifice or to close the orifice after a given time so that the powder flowing through in that time period can be weighed.

Even though the angle of repose measurements and the timed delivery technique give results somehow relatable to flow properties of the material, in the best of cases reproducibility is quite poor.

An explanation for the unsuccess of these tests is that the outlined tests did not hit the focal point of the problem. In particular, it is wrong to identify the flowability with the interparticle friction, as though powders were glass or sand balls.

The truth is that the parameters which determine the flowability of the powder are numerous and with contrasting and interdependent influence: granulometric, "fines", unit surface, shape of particles, actual density, apparent density, porosity, air permeability through powder, electrostatic charge, humidity, dwell, cohesion strengths (such as London, hydrogen, etc.)

Ausburger and Shangraw (J. Pharm. Sci, 55, No. 4, 418–423 (1966)), attempted to evaluate and compare the free flowing properties of powders using the weight and weight variation of the finished tablets as the measured parameter. It was felt in fact that the weight variation of both capsules and tablets is directly dependent upon the reproducibility of powder flow into a fixed volume receptable (which may be a tablet die cavity or a capsule shell) and that good precision, which reflects in a higher tablet weight and a lower coefficient of variation, can only be obtained when the powder to be filled has a good flowability. Even though this method can be conveniently used in routine quality control tests, it is tedious, time consuming and not practical at the preliminary product development stage mainly because it requires a large quantity of drug.

A further method for determining the free flow properties of a powder has been described in DEGUSSA Schriftenreihe, Anwendungstechnik Pigmente Nr. 31 (Wolfgang Hanau (Main)) pages 6 to 8 and is based on how the powder runs through sand timer-like funnels with varying orifices. The equipment there described consists of a series of five glass funnels with orifice diameters of 2.5, 5, 8, 12, and 18 mm, and the powder flowability is ranked as outstanding, very good, good, acceptable or poor depending on the diameter of the orifice which the powder can still pass through. This equipment however only gives a rough estimation of the flowability of a powder, and it does not provide reproductive and precise enough results to be relied upon in the pilot or industrial plants.

SUMMARY OF THE INVENTION

The apparatus described in the present invention provides a new and simple approach to measuring the flowability of a powder at a preliminary laboratory stage. It is based on the ability of a powder to flow through a series of holes of different size in a plate, the diameter of the smallest hole which the powder flows through being the reciprocal of the flowability value. Each run gives a positive result if the flow of the powder begins within 60 seconds and continues until a cavity of conical or cylindrical shape is formed in the whole thickness of the fill.

The equipment of the present invention consists, in its essential features, of a cylinder which is fitted at the bottom with a disk containing a central hole of varying diameter, closed by a removable plate.

The dimensions of the cylinder are not of critical importance. However, for economy and space reasons cylinders of sufficiently reduced size are preferably employed, such as for instance from about 40 to about 100 mm in inside diameter and from about 50 to about 100 mm long.

It is easily intended that the cylinder dimensions must depend on those of the series of holes since the cylinder diameter must be bigger than the largest hole.

Also the material with which the apparatus is made is not critical, provided that the material employed does not impart an electrostatic charge to the powder to be tested since this would influence the results. Preferably, glass, metal and metal alloys are employed.

The diameter of the holes should be suitably selected within a sequence of increasing size and it must be consistent with the purposes of the test. In fact in the pharmaceutical industry powders are preferably employed which freely flow through holes from about 4 to about 34 mm in diameter while for analytical purposes even holes up to 40 mm or more in diameter are also employed.

The sequence of holes must be set up with a large number of holes so as to provide reliable and precise results. The difference in diameter between two consecutive holes may range from about 0.5 to about 3 mm and preferably from about 0.5 to about 2 mm.

In a specific embodiment the equipment is provided with several disks, each one containing a hole of different diameter to be inset in the fixed cylinders. According to said embodiment, the essential components of the equipment are:

(1) A stainless steel cylinder, 58 mm internal diameter, 70 mm high, about 185 ml capacity, for powder loading;

(2) A series of 22 stainless steel drilled disks, 60 mm external diameter, 0.5 mm plate thickness, hole diameter:
4-5-6-7-8-9-10-12-14-16-18-20-22-24-26-28-30-32-34-36-38-40 mm;

(3) a knurled ring containing a disk (2) to be snapped underneath cylinder (1);

(4) A lever device with a 48 mm diameter shutting disk, supported by bearing (5) which acts as a fulcrum for manual shutting and release, instantly and without hole shakes;

(5) A bearing holding and supporting cylinder (1) and acting as fulcrum for lever device (4);

(6) A laboratory bearing to support the system through bearing ((5).

The apparatus is also equipped with:

(7) A series of glass or stainless steel funnels, 70 mm long stems, with a stem bore of from 3 to 15 mm inside diameter. The feed funnel is supported by a ring fixed to bearing (6) so that its tip is directly over the center of the cylinder and just above the surface of the powder fill. These funnels may be substituted by a screen vibrated by a small motor with a very low power rating to avoid the formation of statical electricity; (8) A container which collects the powder flowing through the hole.

Said embodiment is further illustrated by the accompanying drawings wherein:

FIG. 1 is a schematic and isometric view of a flowability test apparatus in its basic design constructed according to the principles and teachings of the invention, the shutting disk 4 in this view being in the open position, FIG. 2 is a top view of the apparatus, FIG. 3 is a side view of the apparatus, the shutting disk 4 in this view being in the closed position and FIG. 4 separately illustrates components 1, 2, 3, and 5 of the assembly described before.

Figure 5:
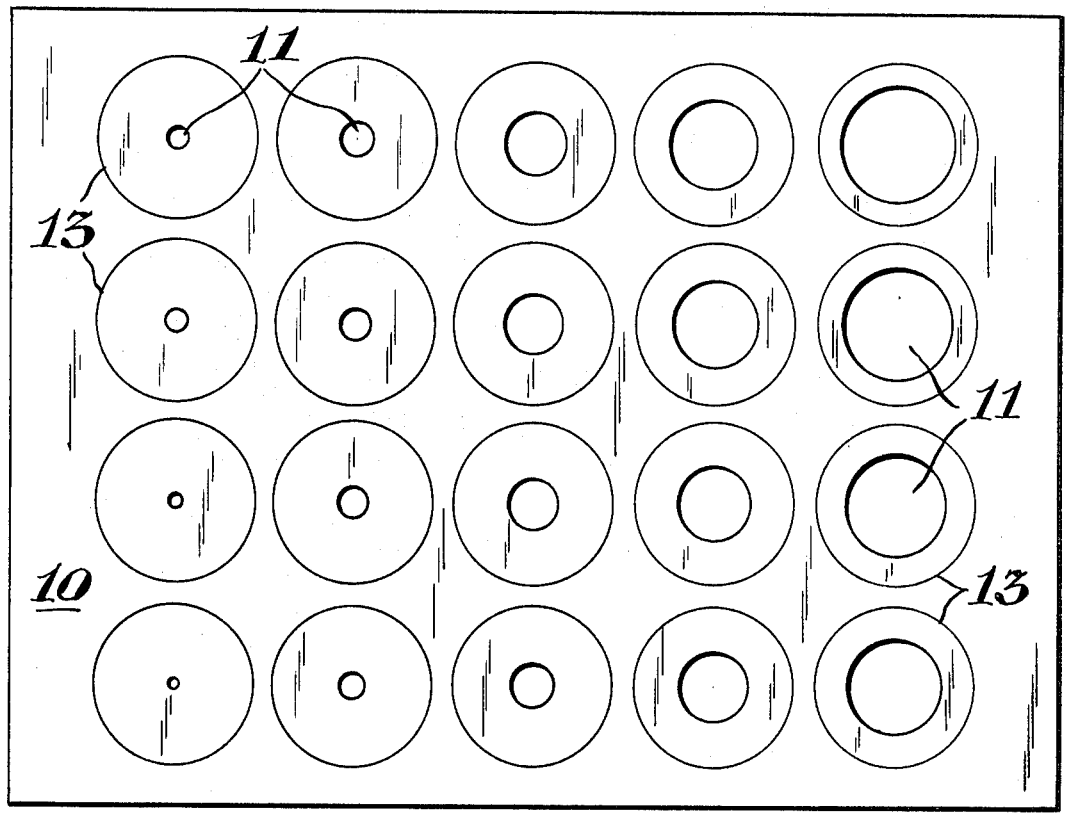

FIG. 5 illustrates an alternative embodiment using a single plate having a plurality of holes 11.

Figure 6:
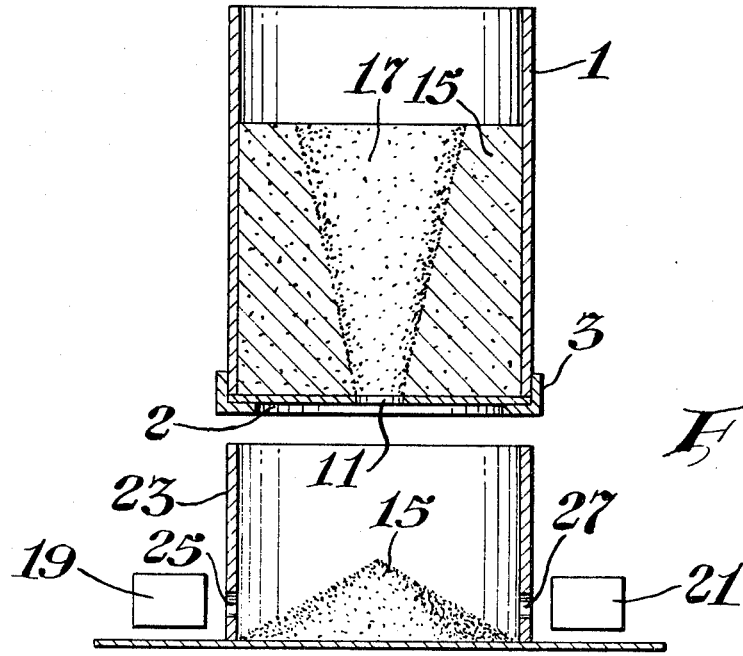

FIG. 6 is a schematic sectional view of a device of the invention after a powder fill 15 has flowed through a hole 11 in a disk 2.

In another embodiment illustrated in FIG. 5, the series of different disks is replaced by a plate 10 having holes 11 distributed in one or more rows over which the open cylinder 1 may be moved. The cylinder 1 is not shown in FIG. 5, however, the position to which the cylinder is to be moved relative to each hole is shown by the concentric circles 13.

In still another specific embodiment the cylinder is closed at the bottom with a fixed disk equipped with a shutter and a mechanical device setting the aperture of the hole. This mechanical device may be manually operated or used aumomaticly. In this second case the diameter of the aperture may be visualized at any time through a registering dial connected to the shutter. Furthermore, said equipment may be fitted with a detecting system, such as a photoelectric cell (including photocell light source 19 and photocell receiver 21, for detecting the interruption of a light beam through apertures 19, 21 in a receiving cylinder 23 by the powder 15) below the test cylinder 1, that stops the shutter 4 when the powder begins to flow, thus allowing a direct reading of the flowability value on the registering dial.

Determinations of powder flowability begins with pouring 50 g of the test powder through a suitably selected funnel 7 in the filling cylinder 1. The criterion used for selecting the proper funnel is that its internal diameter must be the smallest on which still allows free flowing of the powder. Then the shutter is rapidly removed by manually operating on lever 4. As illustrated in FIG. 6, free flowing powder 15 slowly flows even through a small hole 11 until an inverted cone 17 is formed in the whole thickness of the fill 15, while a powder which flocculates into a mass, falls as a lump leaving a cylindrical cavity in the fill. If the run is positive, the powder will be tested again, by using a disk with a smaller hole. Conversely if the run is negative, a larger hole will be tested.

Along these lines we have carried out many measurements testing a number of different powders.

The conclusions which can be drawn on the basis of these experiences are that:

in classical incapsulating machines such as Parke Davis, Zanasi, and MG2, optimum results can be obtained with powders having an intrinsic flowability comprised between 10 and 24, i.e. with powders which freely flow through a hole from 10 to 24 mm in diameter.

As for compressed tablet manufacturing, the optimum range also depends on the diameter of the die punches which are used and is comprised from about 25 to about 100% of said diameter and preferably from about 50 to about 100%. The high correlation between the instrinsic flowability of a blend as measured according to the method of the present invention and the coefficient of variation of the mean weight of capsules filled with the same blend in a pilot plant is illustrated in the following table which collectes some representative experimental data:

| Intrinsic flowability value | Coefficient of variation of the mean weight of type 1 capsules filled with a Zanasi LZ-6 encapsulating machine |
| --- | --- |
| 20 | 0.52 |
| 22 | 1.20 |
| 24 | 1.76 |
| 26 | 2.24 |
| 28 | — |
| 30 | 3.33 |

Powder flowability has been defined as the property of a powder to flow under the influence of gravity and other forces. We will now demonstrate that there is a correlation between the diameter of the smallest hole which the powder still passes through and these forces, thus showing that the assumed correlation between said diameter and flowability (one the reciprocal of the other) is correct. In fact by indicating with k: the internal friction coefficient of the powder, that is to say "coefficient of viscosity" of the powder, expressed in dyne/cm$^2$; with d: the diameter of the hole in cm; with $\delta$: the apparent non-compact density of the powder expressed in gr/cm$^3$; with h: the height of the fill; and with g: the acceleration of gravity (980 cm/sec$^2$);

we may easily write the following equation (1)

$$\pi \cdot \left(\frac{d}{2}\right)^2 \cdot h \cdot \delta \cdot g \geq 2\pi \cdot \left(\frac{d}{2}\right) \cdot h \cdot k \qquad (1)$$

(wherein $$\pi \cdot \left(\frac{d}{2}\right)^2 \cdot h \cdot$$

is the volume of the cylinder and $$2\pi \left(\frac{d}{2}\right)$$

h is the side surface of the cylinder of powder) which simly indicates that the weight of the cylinder of the falling powder must be greater than the friction on the side surface of the cylinder itself.

To simplify we obtain (2)

$$d \geq \frac{4k}{\delta \cdot g} \qquad (2)$$

and considering the smallest hole which still allows the powder to flow freely, we may approximate the above equation to the threshold value (3):

$$d_{smallest\ hole} = \frac{4k}{\delta \cdot g} \qquad (3)$$

Since it is quite evident that the longer the hole, the less the flowability of the powder and viceversa, we will express the flowability as the reciprocal of the diameter of the smallest hole and therefore as $$\frac{1}{d_{s,h}} = \frac{\delta \cdot g}{4k} \qquad (4)$$

Flowability, according to expression (4), will depend directly from the apparent density and the "coefficient of viscosity", which in their turn are influenced by other factors which, as such, do not appear in the formula, such as electrostatic charge and humidity.

What is claimed is:

1. A powder flowability test device which essentially consists in a cylinder which is fitted at the bottom with a disk containing a central hole of varying diameter closed by a removable plate, said cylinder having an inside diameter which is larger than the largest hole diameter.

2. A powder flowability test device as claimed in claim 1 characterized in that it comprises several disks, each one containing a hole of different diameter to be inset in the fixed cylinder.

3. A powder flowability test device as claimed in claim 1 characterized in that it comprises a plate containing several holes of different diameter distributed in one or more rows over which the open cylinder may be moved.

4. A powder flowability test device of claim 2 wherein the diameters of the holes are selected within a sequence of increasing size comprised from about 4 to about 40 mm, and the difference in diameter between two consecutive holes ranges from about 0.5 to about 3 mm.

5. A powder flowability test device as claimed in claims 1 including a detecting system that stops the shutter when the powder begins to flow.

6. A powder flowability test device as claimed in claim 5 wherein the detecting system is a photoelectric cell.

7. A powder flowability test device comprising a horizontal plate for supporting a powder fill, said plate having a hole of variable diameter; means for containing the powder fill on the plate over the hole, said means having dimensions larger than the largest hole diameter; and means for shutting said hole, said shutting means being releasable to open said hole, thereby allowing powder to flow through the hole without shaking the hole; whereby a cavity is formed in the powder fill on the plate when the powder flows through said hole.

8. A method of measuring intrinsic flowability of a powder comprising: (a) disposing a powder fill on a plate having a closeable hole therethrough; (b) opening the hole to allow powder above the hole to flow therethrough; (c) observing the resulting formation of a cavity in the powder fill when powder flows through the hole; (d) repeating steps (a) through (c) with a smaller hole when powder flow occurs, and repeating steps (a) through (c) with a larger hole when powder flow does not occur; and (e) determining the size of the smallest hole through which the powder flows until a cavity is formed in the powder fill.

9. Method of claim 11 wherein the cavity in step (e) is a cavity of conical or cylindrical shape in the whole thickness of the fill.

* * * * *